United States Patent
Grossnickle et al.

(10) Patent No.: US 9,042,516 B2
(45) Date of Patent: May 26, 2015

(54) NONDESTRUCTIVE EXAMINATION OF STRUCTURES HAVING EMBEDDED PARTICLES

(71) Applicant: The Boeing Company, Chicago (IL)

(72) Inventors: James A. Grossnickle, Bellevue, WA (US); Robert B. Greegor, Auburn, WA (US)

(73) Assignee: The Boeing Company, Chicago, IL (US)

(*) Notice: Subject to any disclaimer, the term of this patent is extended or adjusted under 35 U.S.C. 154(b) by 127 days.

(21) Appl. No.: 13/647,423

(22) Filed: Oct. 9, 2012

(65) Prior Publication Data
US 2014/0098936 A1    Apr. 10, 2014

(51) Int. Cl.
*G01N 23/04* (2006.01)
*G01N 23/087* (2006.01)

(52) U.S. Cl.
CPC ....... *G01N 23/087* (2013.01); *Y10T 428/24917* (2015.01); *G01N 2223/607* (2013.01); *G01N 2223/615* (2013.01)

(58) Field of Classification Search
USPC ......................................................... 378/58
See application file for complete search history.

(56) References Cited

U.S. PATENT DOCUMENTS

| | | | |
|---|---|---|---|
| 3,412,243 A | 11/1968 | Williams et al. | |
| 3,956,631 A | 5/1976 | Crosby, Jr. | |
| 5,483,571 A | 1/1996 | Madaras | |
| 5,641,422 A | 6/1997 | Matsen et al. | |
| 5,833,795 A | 11/1998 | Smith et al. | |
| 6,127,822 A | 10/2000 | Sasahara et al. | |
| 6,849,195 B2 | 2/2005 | Basheer | |
| 8,043,982 B2* | 10/2011 | Telander | 442/134 |
| 2005/0282300 A1* | 12/2005 | Yun et al. | 438/14 |
| 2009/0184261 A1 | 7/2009 | Ein-Gal | |
| 2012/0180928 A1 | 7/2012 | Bruck | |

FOREIGN PATENT DOCUMENTS

| | | |
|---|---|---|
| DE | 103 22 055 A1 | 12/2004 |
| JP | 06-155583 A | 6/1997 |
| WO | WO2009032809 | 3/2009 |

OTHER PUBLICATIONS

Chen et al., "Metal-bonded Co-Ferrite Composites for Magnetostrictive Torque Sensor Applications" IEEE Transactions on Magnetics, vol. 35, No. 5, (Sep. 1999), pp. 3652-3654.

Chen et al., "Health monitoring of composites embedded with magnetostrictive thick film without disassembly," Inst. of Physics Publishing, SmartMater.Struct.15(2006) 20-32.

Grimes et al., "Wireless Magnetoelastic Resonance Sensors: A Critical Review" Sensors 2002, 2, 294-313.

Pasquale et al., "Stress sensing with Cobased ferrite composites," Journal of Magnetism and Magnetic Materials 242-245 (2002) 1460-1463.

Saravanos et al., "Detection of Delaminations in Composite Beams Using Piezoelectric Sensors," NASA Technical Memorandum 106611 (Jun. 1994).

(Continued)

*Primary Examiner* — Phillip A Johnston
(74) *Attorney, Agent, or Firm* — Hugh P. Gortler

(57) ABSTRACT

A system comprises a structure having particles embedded at a level within the structure, and X-ray imaging apparatus for capturing images of the particles at the level.

21 Claims, 5 Drawing Sheets

(56) References Cited

OTHER PUBLICATIONS

Tan et al.,"Delamination Detection of a Laminated Beam Using Magnetostrictive Composite Sensor and Actuator," Journ. of Reinforced Plastics & Composites, 26-8 (2007) 831-46.

Jordan et al. "Microradiographic strain measurement using markers," Experimental Mechanics, vol. 34, No. 2, Jun. 1994, pp. 155-165.

Germnaneau et al. "Comparison between X-ray micro-computed tomography and optical scanning tomography for full strain measurement by digital volume correlation," NDT&E International, vol. 41, No. 6, Sep. 2008, pp. 407-415.

Bay et al., "Digital volume correlation: three-dimensional strain mapping using X-ray tomography," vol. 39, No. 3, Sep. 1999, pp. 217-226.

* cited by examiner

NONDESTRUCTIVE EXAMINATION OF STRUCTURES HAVING EMBEDDED PARTICLES

BACKGROUND

Nondestructive examination (NDE) may be used to evaluate properties of composite structures. For instance, NDE such as ultrasonic testing may reveal internal structural inconsistencies such as voids, wrinkles, cracks and delaminations.

However, ultrasonic testing does not reveal internal strains within composite structures. Other techniques may determine strains at the surface or bulk of composite structures, but not within the composite structures.

It would be desirable to nondestructively determine strains within composite structures.

SUMMARY

According to an embodiment herein, a system comprises a structure having particles embedded at a level within the structure, and X-ray imaging apparatus for capturing images of the particles at the level.

According to another embodiment herein, a method of performing nondestructive examination on a structure having embedded particles comprises illuminating the structure with X-rays; forming an image of the illuminated structure, the image showing the particles; and determining displacements of the particles in the image.

According to another embodiment herein, a laminate comprises a plurality of plies of reinforcing fibers in a matrix. The matrix contains patterns of metal particles embedded within different plies, wherein the particles embedded in the different plies differ by at least one of nominal size and composition.

These features and functions may be achieved independently in various embodiments or may be combined in other embodiments. Further details of the embodiments can be seen with reference to the following description and drawings.

DETAILED DESCRIPTION

Figure 1:
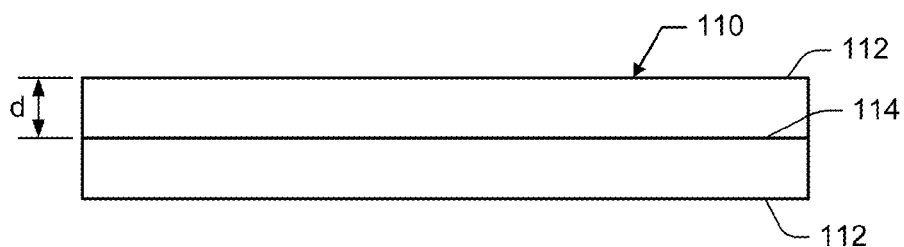
FIG. 1 is an illustration of a structure including embedded particles.

Reference is made to FIG. 1, which illustrates a structure 110 including embedded particles. In some embodiments, the structure 110 may be a composite laminate composed of a plurality of plies of reinforcing fibers embedded in a matrix. For instance, the laminate may include multiple plies of carbon reinforcing fibers embedded in a plastic matrix. In FIG. 1, each element 112 represents multiple plies. In other embodiments, the structure 110 may include two or more members 112 (e.g., rigid composite members) that are adhesively bonded together at a bond line.

The particles are embedded at a level 114 below a surface of the structure 110. As shown in FIG. 1, the level 114 is at a depth (d) below the surface. For a structure 110 including members 112 adhesively bonded together at a bond line, the particles may be embedded in the bond line. That is, the bond line is at a depth (d) below the surface. For a structure 110 including a plurality of laminated plies 112, the particles may be embedded in one or more of the plies. That is, the ply or plies containing the embedded particles are a depth (d) below the surface.

The embedded particles are made of a material that is not completely transparent to X-rays. For instance, the embedded particles may fluoresce, scatter or absorb X-rays. In some embodiments, the particles may be metal particles. The particles may be micron-sized or smaller.

Figure 2A:
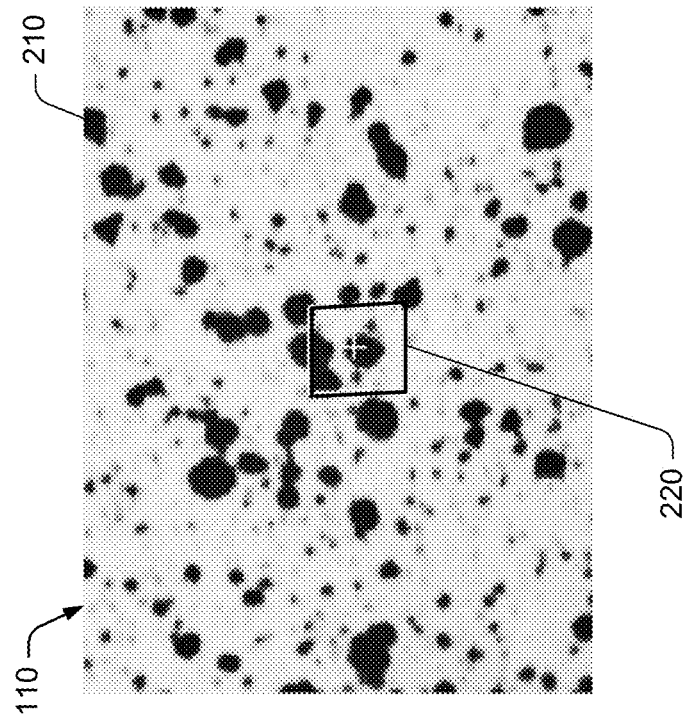
FIGS. 2A and 2B are illustrations of particles embedded within a structure before and after the structure has undergone stress.

Reference is now made to FIG. 2A, which shows a plurality of embedded particles 210. The particles 210 are arranged in a pattern that is non-uniform and irregular. In some embodiments, the particles 210 may be arranged in clumps. In other embodiments, the particles 210 may be arranged in a stochastic pattern. For example, the particles 210 may be arranged in a stochastic speckle pattern.

The structure 110 may undergo stress from external forces and/or internal forces (e.g., by temperature cycling). The stress causes strain in the structure 110. In laminates made of composite fiber reinforced plastic (CFRP), for instance, the strain may cause deformations or internal inconsistencies such as voids, wrinkles, cracks and delaminations.

Figure 3:
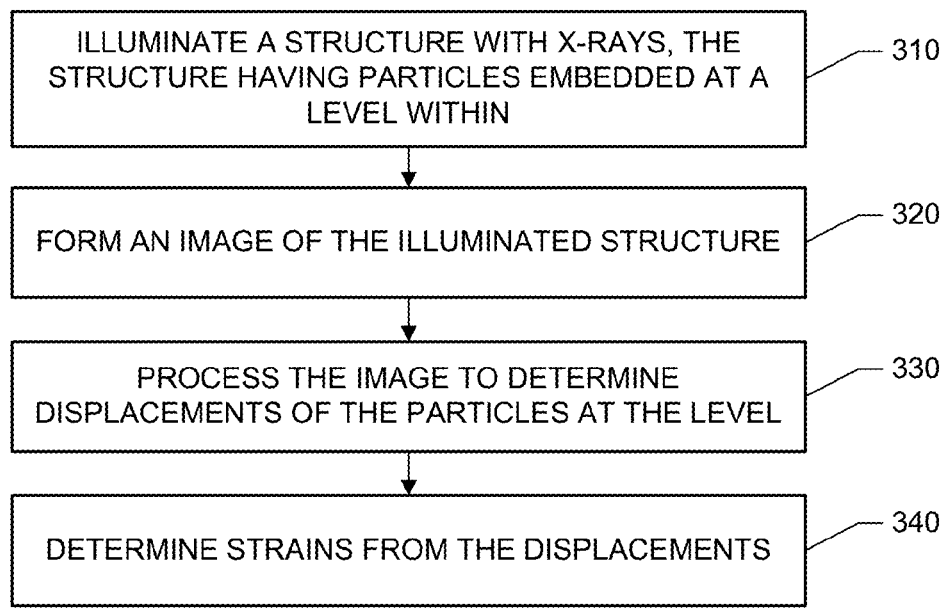
FIG. 3 is an illustration of a method of determining strain within a structure having embedded particles.

Reference is now made to FIG. 3, which illustrates a method of determining strains within a structure having particles embedded particles therein, where the particles are not completely transparent to X-rays. At block 310, the structure is illuminated with X-rays. Except for the particles, the structure may fully transmit the X-rays. The particles prevent the X-rays from being fully transmitted. For instance, the particles may fluoresce, scatter or absorb the X-rays, or they may reflect the X-rays (e.g., at grazing incidence).

At block 320, an image of the illuminated structure is formed. The image shows a pattern of particles at a level within the structure.

At block 330, the image is processed to determine displacements of the particles at different locations at the level. At block 340, strains are computed from the displacements.

Figure 2B:
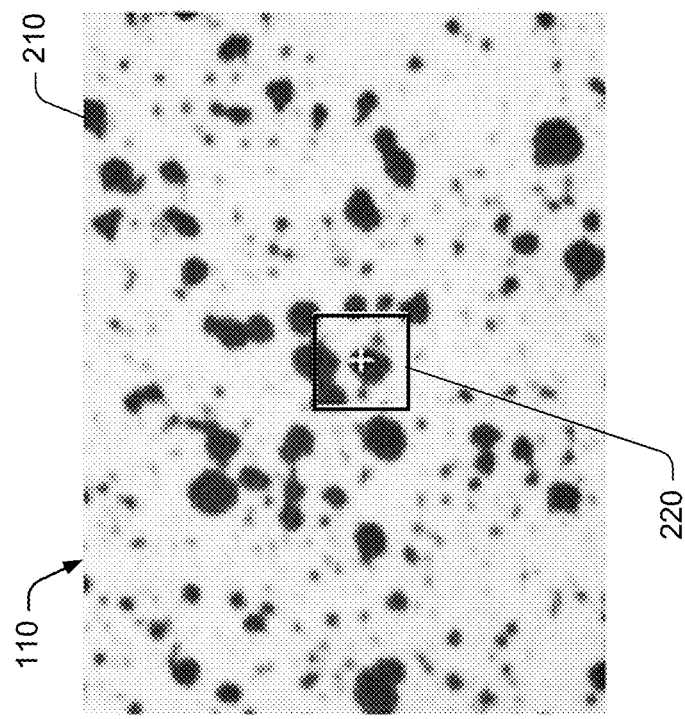

Reference is made to FIGS. 2A and 2B, which illustrate particles 210 embedded at a level within the structure 110. Assume FIG. 2A is a baseline image of the particles 210 prior to the structure 110 undergoing stress, and assume FIG. 2B is an image of the particles after the structure 110 has undergone stress. A pixel block 220 encompasses several particles 210. Notice the skewing of the pixel block 220 in FIG. 2B. The skewing indicates that the particles 210 within the pixel block 220 have been displaced as a result of the stress.

Displacements and strains may be computed by digital image correlation (DIC). DIC is an optical method that employs tracking and image registration techniques for accurate measurements of changes in images. DIC may perform pattern recognition on multiple images. Each image may be broken up into blocks of pixels (e.g., 15×15 pixel blocks, 25×25 pixel blocks 15×20 pixel blocks) that cover a certain number (e.g., five to seven) particles. These blocks of pixels are found in all of the images, and then the shape of each pixel block in each image is determined. The change of shape of each block of pixels determines a displacement at a location at the level. In this manner, displacements are determined at different locations at the level.

A set of strains may then be computed at each block center. A strain field for the level may be formulated as a matrix of the strains. Interior modulus properties may also be determined from stress versus strain curves in the elastic region of the material.

Figure 4:
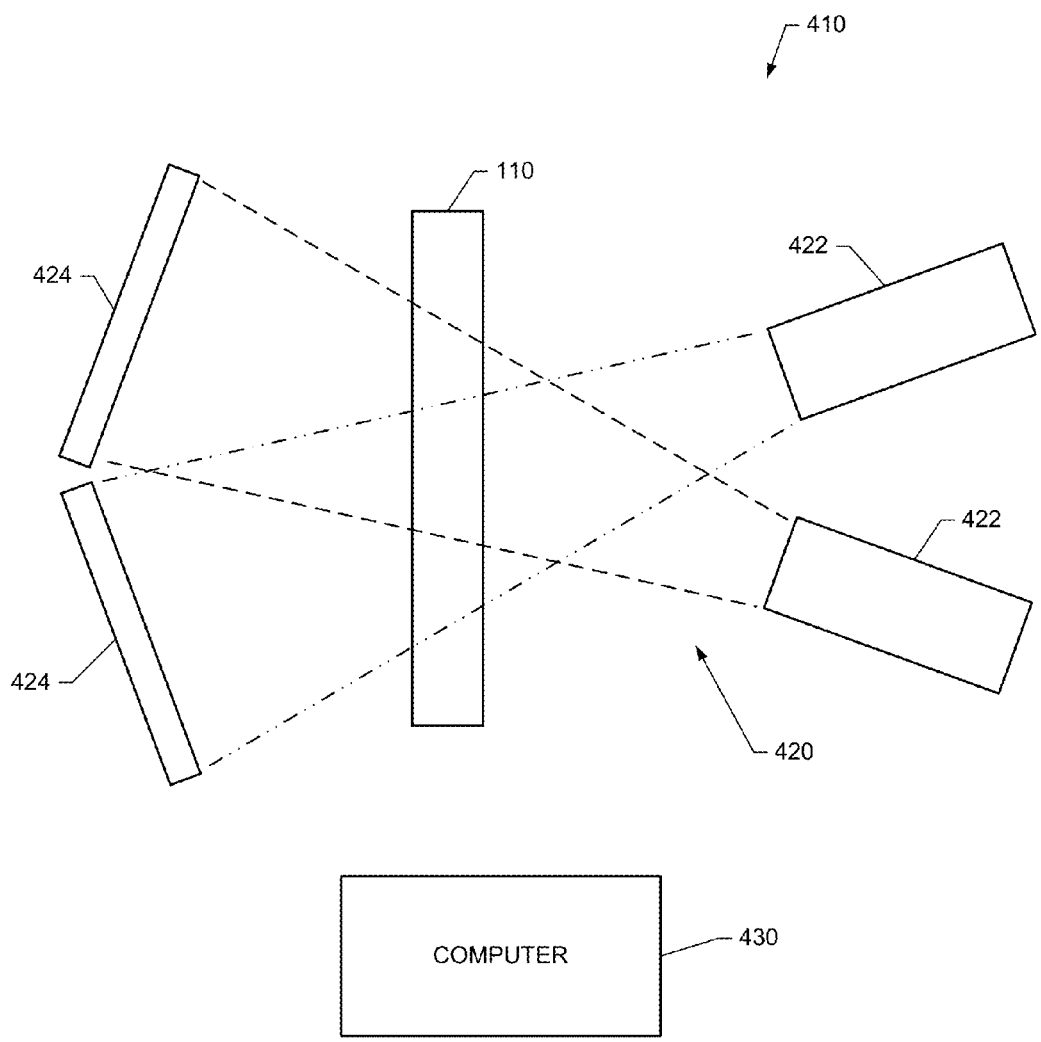
FIG. 4 is an illustration of a system for determining strain within a structure having embedded particles.

Reference is now made to FIG. 4, which illustrates a system 410 for determining strains at a level within a structure 110, where particles are embedded at that level. The system 410 includes imaging apparatus 420 for capturing images of the particles within the structure 110. The imaging apparatus 420 of FIG. 4 includes first and second X-ray sources 422 and first and second X-ray detectors 424. The sources 422 may provide collimated X-rays. If the particles block the X-rays, the detectors may include semiconductor detectors that convert X-rays to electrical signals or semiconductor detectors that convert X-rays to visible light, which is then converted to electric signals. If the particles fluoresce in response to the X-rays, the image may be formed by energy dispersive detection.

High contrast in the images is desirable. Distances between the sources 422, the structure 110, and the detectors 424 may be adjusted to give the proper field of view and best contrast.

The first and second detectors 424 may be oriented at an angle with respect to the particles to create depth perception in the images. Depth perception, in turn, enables structural inconsistencies such as internal delaminations to be identified.

A system herein is not limited to two detectors. Some embodiments may include only a single detector. Others may include more than two detectors.

The system 410 further includes a computer 430 programmed to process the images created by the detectors 424. The processing includes digital image correlation of the pixel blocks of particles within the images. The computer 430 may be programmed with a commercial off the shelf DIC software, such as ARAMIS software.

In some embodiments, the computer 430 may be further programmed to identify internal structural inconsistencies from the strain field. For example, the strain field may be compared to baseline data corresponding to different types of structural inconsistencies. In other embodiments, skilled technicians may analyze the strain field to identify structural inconsistencies.

Figure 5:
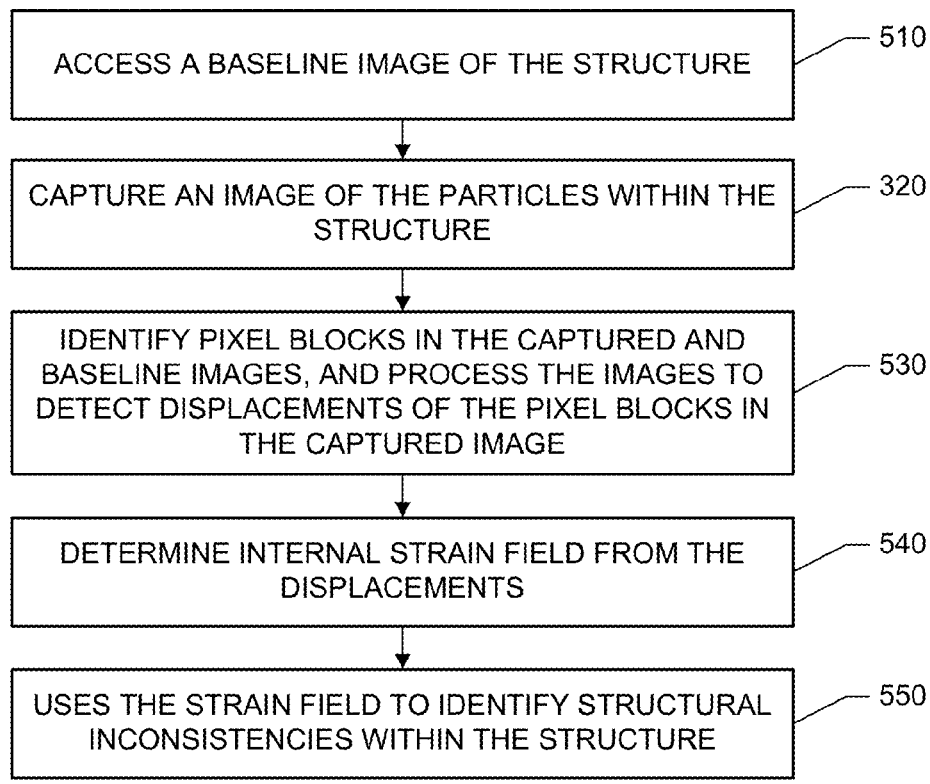
FIG. 5 is an illustration of a method of using the system of FIG. 4.

FIG. 5 is an illustration of a method of using the system of FIG. 4 to perform nondestructive inspection on a structure having particles embedded at a level. At block 510, the computer 430 accesses a baseline image of the structure. The baseline image represents a "healthy" structure. The baseline image may be been taken before the structure was placed into service, or it may be taken at a later time after having been stressed.

At block 520, the computer 430 commands the imaging apparatus 420 to capture one or more images of the particles within the structure 110. At block 530, the computer 430 processes the captured and baseline images to detect displacement of a number of pixel blocks at each level. Several pixel blocks may be used to determine the value of displacement at a given location.

At block 540, the computer 430 determines strains from the pixel block displacements, and formulates a strain field at the level. If the structure 110 includes two parts bonded together at a bond line, and the particles are embedded in the bond line, then a strain field would be determined at the level of the bond line. If the structure 110 is a laminate, and one of the plies is embedded with particles, then a strain field would be determined at the level of that ply.

At block 550, the strain field is used to identify internal structural inconsistencies such as voids, wrinkles, delaminations and cracks. For example, a delamination would manifest as a change in out of plane displacement (in a 3D image), while a crack or wrinkle would manifest as a large localized strain.

A structure herein is not limited to particles at a single level. In some embodiments, a structure may include particles embedded at multiple levels.

Figure 6:
FIG. 6 is an illustration of a multi-ply structure including embedded particles at multiple levels.

FIG. 6 is an illustration of a laminate 610 including metal particles embedded at multiple levels. Different types of particles are embedded in different plies. The type of particle may differ by nominal size and/or composition. As but one example, one ply 612 may be embedded with copper particles, another ply 614 may be embedded with titanium particles, another ply 616 with aluminum particles, and so on. Other metals include, but are not limited to, gold, silver, tungsten, and iron. Other plies 618 of the structure do not contain particles that affect the X-rays.

FIG. 6 shows every other layer being imbedded with metal particles. In practice however, there may be greater separation between plies having embedded particles. As but one example, in a laminate having thirty plies, one of every six plies may contain metal particles.

Figure 7:
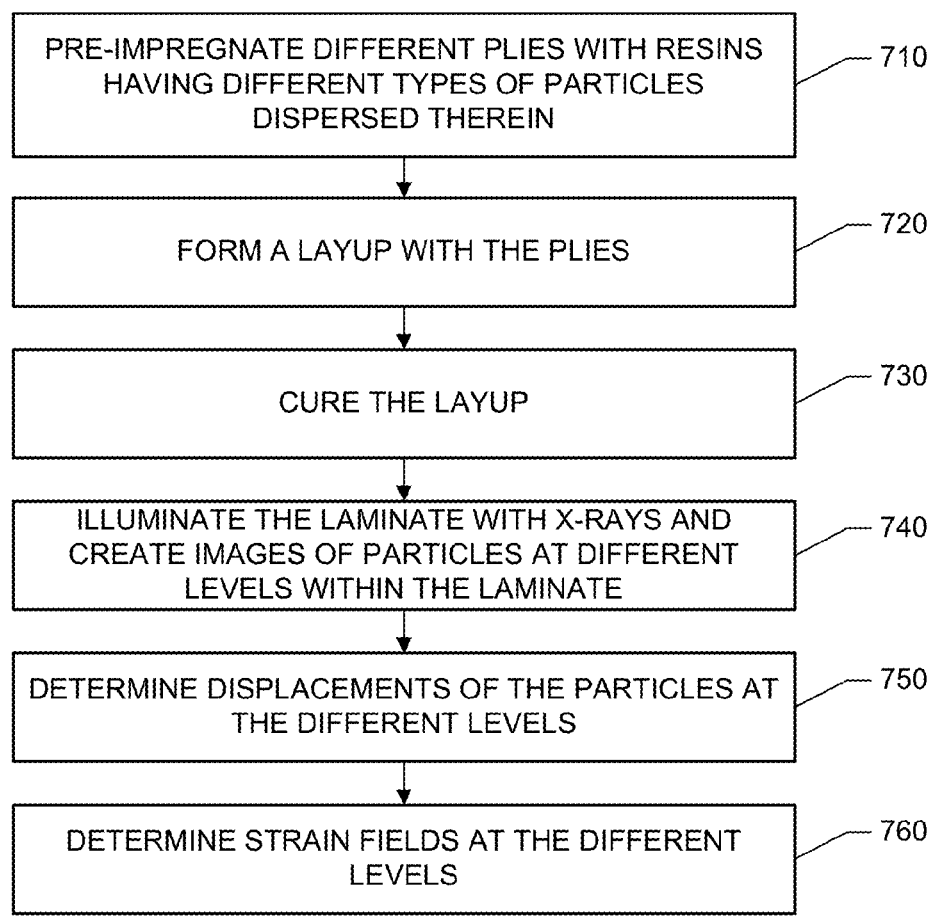
FIG. 7 is an illustration of a method of fabricating and nondestructively examining a CFRP laminate.

Reference is now made to FIG. 7, which illustrates the fabrication and nondestructive examination of a CFRP laminate. Prior to layup, the different plies of the laminate are pre-impregnated with resins having different types of particles dispersed therein (block 710). Those plies not containing particles are impregnated with resin. During layup of the laminate (block 720), the pre-impregnated plies may be deposited on a forming tool.

After the layup has been cured (block 730), nondestructive examination is performed. During nondestructive examination, the laminate is illuminated with X-rays and the particles at different levels are imaged (block 740). In some embodiments, the levels may be illuminated sequentially at different X-ray energy levels, thereby creating images of different levels. In other embodiments, the different levels may be illuminated and imaged in a single pass. Particles at different levels may be differentiated by the amount of energy they absorb. For example, lead particles will absorb more energy than titanium particles and, consequently, will have a lower grayscale value in the image.

In other embodiments, the different particles absorb the X-rays and fluoresce at different frequencies. Images of the different levels may be formed by energy dispersive detection, which would allow discrimination of the florescent spectra of the different particles. For example, the florescent spectra of titanium, copper, tungsten, and lead are dispersed at different levels.

Using DIC, the displacement of the metal particles in the image is determined at different locations for each of the different levels (block 750). Strain fields are computed for the different levels (block 760).

The invention claimed is:
1. A system comprising
 a structure having particles embedded at different levels within the structure, wherein the particles at the different levels differ by at least one of nominal size and composition;
 X-ray imaging apparatus for capturing images of the particles; and a computer programmed to analyze the images to determine strains at different locations at the different levels.

2. The system of claim 1, further comprising identifying internal structural inconsistencies from the strains.

3. The system of claim 1, wherein determining the strains includes forming pixel blocks containing the particles, and determining changes in shape of the pixel blocks.

4. The system of claim 1, wherein the computer is programmed to perform digital image correlation of the particles in the images.

5. The system of claim 1, wherein the imaging apparatus includes first and second X-ray sources on one side of the structure and at least one X-ray detector on an opposite side of the structure.

6. The system of claim 1, wherein the particles are arranged in a non-uniform, irregular pattern.

7. The system of claim 1, wherein the particles are metal particles.

8. The system of claim 1, wherein the structure includes first and second members joined by a layer of adhesive, the adhesive layer containing a pattern of the particles.

9. The system of claim 1, wherein the structure includes a laminate and wherein the particles are embedded in at least two plies of the laminate.

10. The system of claim 1, wherein the structure includes a plurality of plies of reinforcing fibers embedded in a matrix; and wherein the different levels are formed by the plurality of plies; whereby different types of the particles are embedded in different plies within the structure.

11. A method of performing nondestructive examination on a structure having embedded particles, the particles embedded at a level within the structure, the method comprising:

Illuminating the structure with X-rays;

forming an image of the illuminated structure, the image showing the particles;

determining displacements of the particles in the image; and determining strains from the displacements.

12. The method of claim 11, wherein the particles are illuminated to fluoresce, scatter, or absorb the X-rays.

13. The method of claim 11, wherein determining the displacements includes determining shape changes of pixel blocks in the image.

14. The method of claim 11, wherein forming the image includes using, first and second detectors at an angle with respect to the particles to create depth in the image.

15. The method of claim 11, wherein a computer is used to perform digital image correlation (DIC) to determine the displacement of the particles.

16. The method of claim 14, further comprising identifying internal structural inconsistencies from the strains.

17. The method of claim 11, wherein the particles are embedded in multiple plies, wherein the particles embedded in the different plies differ by the nominal size and/or composition; wherein the different plies having embedded particles are illuminated at different X-ray energy levels; and wherein the displacement of the particles in the image is determined for each ply having embedded particles.

18. The method of claim 11, wherein the particles are embedded in different plies, wherein the particles embedded in the different plies differ by the nominal size and/or composition; wherein the different plies having embedded particles are illuminated to fluoresce, and wherein forming the image includes using energy dispersive detection to image the fluorescing particles.

19. A laminate comprising a plurality of plies of reinforcing fibers in a matrix, the matrix containing patterns of metal particles embedded within different plies, wherein the particles embedded in the different plies differ by at least one of nominal size and composition.

20. The laminate of claim 19, wherein the particles embedded in the different plies differ by composition.

21. The laminate of claim 19, wherein the particles embedded in the different plies are arranged in non-uniform, irregular patterns.

* * * * *